United States Patent
Cohen et al.

(10) Patent No.: US 11,344,245 B2
(45) Date of Patent: May 31, 2022

(54) VISUALLY DIFFERENTIATING PRIMARY AND SECONDARY ACTIVATIONS ON ELECTROPHYSIOLOGICAL MAPS

(71) Applicant: BIOSENSE WEBSTER (ISRAEL) LTD., Yokneam (IL)

(72) Inventors: Benjamin Cohen, Haifa (IL); Aharon Turgeman, Zichron Ya'acov (IL); Assaf Cohen, Kiryat Bialik (IL); Eliyahu Ravuna, Kiryat Ata (IL); Natan Sharon Katz, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 86 days.

(21) Appl. No.: 16/437,090

(22) Filed: Jun. 11, 2019

(65) Prior Publication Data

US 2020/0390353 A1    Dec. 17, 2020

(51) Int. Cl.
| | |
|---|---|
| *A61B 5/339* | (2021.01) |
| *A61B 5/00* | (2006.01) |
| *A61B 5/35* | (2021.01) |
| *A61B 5/283* | (2021.01) |
| *A61B 5/333* | (2021.01) |

(52) U.S. Cl.
CPC .............. *A61B 5/339* (2021.01); *A61B 5/283* (2021.01); *A61B 5/333* (2021.01); *A61B 5/35* (2021.01); *A61B 5/7203* (2013.01); *A61B 5/743* (2013.01)

(58) Field of Classification Search
CPC ....... A61B 5/042; A61B 5/0432; A61B 5/044; A61B 5/04525; A61B 5/7203; A61B 5/743; A61B 5/339; A61B 5/35; A61B 5/283; A61B 5/333; A61B 5/6852; A61B 5/0044; A61B 5/062; A61B 5/063; A61B 5/0035; A61B 5/6869; A61B 5/7425; G06T 11/40

See application file for complete search history.

(56) References Cited

U.S. PATENT DOCUMENTS

| | | | |
|---|---|---|---|
| 2008/0188765 A1* | 8/2008 | Stolarski | A61B 5/35 600/518 |
| 2010/0268059 A1 | 10/2010 | Ryu et al. | |
| 2012/0157804 A1 | 6/2012 | Rogers et al. | |

(Continued)

OTHER PUBLICATIONS

Arora, R., Kadish, K. "Fundamentals of Intracardiac Mapping" in: Huang, S.K.S., Wood, M.A., Catheter Ablation of Cardiac Arrhythmias (Philadelphia, PA, Elsevier, 2006), pp. 107-134 (Year: 2006).*

(Continued)

*Primary Examiner* — Mallika D Fairchild
*Assistant Examiner* — Shreya Anjaria
(74) *Attorney, Agent, or Firm* — Dergosits & Noah LLP; Todd A. Noah

(57) ABSTRACT

A method includes receiving an anatomical map of at least a portion of a heart. Positions and respective bipolar intracardiac electrogram (EGM) signals measured at the positions are received for at least a region of the anatomical map. Primary activations and secondary activations are identified in the bipolar intracardiac EGM signals. A surface representation of the bipolar intracardiac EGM signals over the region is derived, including the identified primary activations and secondary activations. The surface representation is presented overlaid on the anatomical map.

10 Claims, 2 Drawing Sheets

(56) References Cited

U.S. PATENT DOCUMENTS

| | | | |
|---|---|---|---|
| 2012/0237093 A1 | 9/2012 | Turgeman | |
| 2015/0141765 A1 | 5/2015 | Razavi et al. | |
| 2016/0022375 A1 | 1/2016 | Blake et al. | |
| 2017/0281031 A1* | 10/2017 | Houben | A61B 18/1492 |
| 2017/0360319 A1 | 12/2017 | Hagfors et al. | |
| 2020/0085329 A1* | 3/2020 | Markovitz | A61B 5/349 |

OTHER PUBLICATIONS

Arora, R., Kadish, K. "Fundamentals of Intracardiac Mapping" in: Huang, S.K.S., Wood, M.A., Catheter Ablation of Cardiac Arrhythmia</i>s (Philadelphia, PA, Elsevier, 2006), pp. 107-134 (Year: 2006).*
U.S. Appl. No. 16/228,426, filed Dec. 20, 2018.
European Search Report for corresponding EPA No. 20179139.9 dated Nov. 11, 2020.
G. Lee et al., "Epicardial wave mapping in human long-lasting persistent atrial fibrillation: transient rotational circuits, complex wavefronts, and disorganized activity", European Heart Journal, vol. 35, No. 2, Aug. 8, 2013, pp. 86-97.

* cited by examiner

VISUALLY DIFFERENTIATING PRIMARY AND SECONDARY ACTIVATIONS ON ELECTROPHYSIOLOGICAL MAPS

FIELD OF THE INVENTION

The present invention relates generally to electrophysiological mapping, and particularly to visualization of cardiac electrophysiological maps.

BACKGROUND OF THE INVENTION

Methods for visualizing mapped cardiac electrophysiological (EP) signals were previously proposed in the patent literature. For example, U.S. Patent Application Publication 2010/0268059 describes a method that includes accessing cardiac information acquired via a catheter located at various positions in a venous network of a heart of a patient. The cardiac information comprises position information, electrical information and mechanical information. The method also maps local electrical activation times to anatomic positions to generate an electrical activation time map. The method maps local mechanical activation times to anatomic positions to generate a mechanical activation time map. The method further generates an electromechanical delay map by subtracting local electrical activation times from corresponding local mechanical activation times, and renders at least the electromechanical delay map to a display.

As another example, U.S. Patent Application Publication 2012/0237093 describes a method consisting of formulating a one-to-one correspondence between locations on a three-dimensional surface of a body cavity and coordinates in a two-dimensional coordinate frame representative of the locations. The method also includes recording respective time-varying electrical potentials at the locations. The method further includes displaying a map of the two-dimensional coordinate frame, and presenting respective graphic representations of the time-varying electrical potentials at positions in the map corresponding to the coordinates of the locations. In an embodiment, the graphic representations comprise rectangular bars having lengths selected in response the electrical potentials. In another embodiment, the graphic representations comprise bars having colors selected in response the electrical potentials.

SUMMARY OF THE INVENTION

An embodiment of the present invention provides a method, including receiving an anatomical map of at least a portion of a heart. Positions and respective bipolar intracardiac electrogram (EGM) signals measured at the positions are received for at least a region of the anatomical map. Primary activations and secondary activations are identified in the bipolar intracardiac EGM signals. A surface representation of the bipolar intracardiac EGM signals over the region is derived, including the identified primary activations and secondary activations. The surface representation is presented overlaid on the anatomical map.

In some embodiments, presenting the surface representation includes presenting the primary activations using a first type of visual indicator and presenting the secondary activations using a second type of visual indicator.

In some embodiments, the first and second types of the visual indicators include first and second different geometrical shapes. In other embodiments, the first and second types of the visual indicators have first and second different colors.

In an embodiment, the first and second types of the visual indicators represent Local Activation Times (LAT).

In another embodiment, identifying the primary activations and the secondary activations in a bipolar intracardiac EGM signal among the bipolar intracardiac EGM signals includes (a) selecting a noise level for the bipolar intracardiac EGM signal, (b) labeling local maxima of the bipolar intracardiac EGM signal, which are above the selected noise level, as activations, and (c) for a given cardiac cycle, labeling an activation having a maximum absolute value as a primary activation, and labeling other activations as secondary activations.

There is additionally provided, in accordance with an embodiment of the present invention, a system, including a memory and a processor. The memory is configured to store an anatomical map of at least a portion of a heart. The processor is configured to (i) receive, for at least a region of the anatomical map, positions and respective bipolar intracardiac electrogram (EGM) signals measured at the positions, (ii) identify in the bipolar intracardiac EGM signals primary activations and secondary activations, (iii) derive a surface representation of the bipolar intracardiac EGM signals over the region, including the identified primary activations and secondary activations, and (iv) present the surface representation overlaid on the anatomical map.

The present invention will be more fully understood from the following detailed description of the embodiments thereof, taken together with the drawings in which:

DETAILED DESCRIPTION OF EMBODIMENTS

Overview

Figure 1:
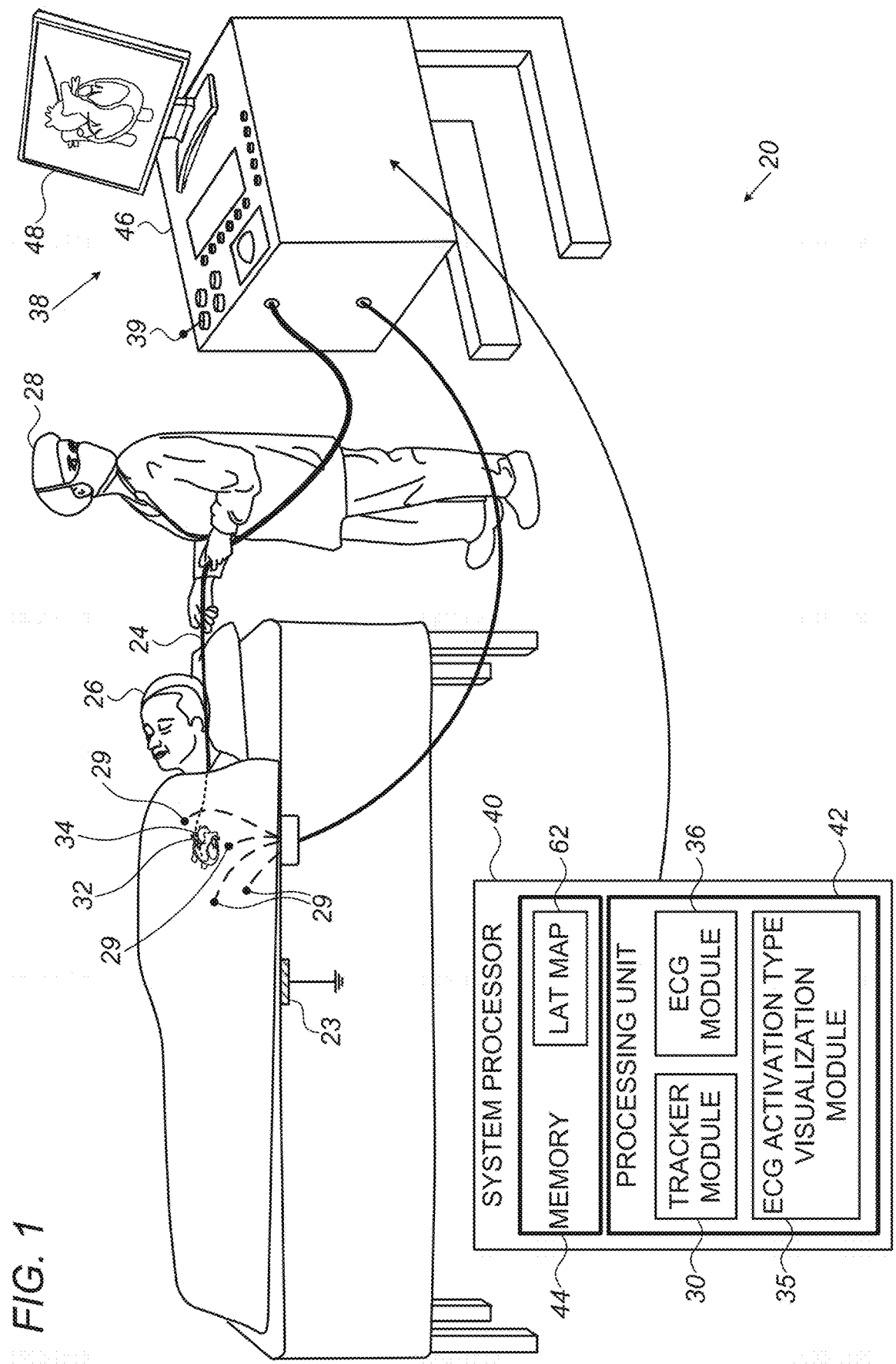
FIG. 1 is a schematic, pictorial illustration of a cardiac three-dimensional (3D) navigation and electrophysiological (EP) signal analysis system, in accordance with an embodiment of the present invention.

In order to characterize cardiac electrophysiological (EP) abnormalities of a patient, a catheter-based EP mapping system may be used to generate an EP map of at least part of the heart of the patient, such as a cardiac chamber. In a typical catheter-based EP mapping procedure, a distal end of a catheter, which comprises sensing-electrodes, is inserted into the heart to sense EP signals. As a physician operating the system moves the distal end inside the heart, the EP mapping system acquires EP signals at various cardiac locations, as well as the respective positions of the distal end. Based on these acquired signals, a processor of the mapping system generates the required EP map.

In some cases, the processor of the EP mapping system presents the measured EP map overlaid on a heart anatomy visualized by, for example, a volume (3D) rendering of at least a portion of the heart. Such an EP overlay rendering may be very useful in diagnosing cardiac irregularities. For example, bipolar intracardiac electrogram (EGM) amplitudes in the form of sails or bars overlaid on an anatomical map may be used, where the height of the sails or bars gives a measure of the bipolar intracardiac EGM signal amplitude at the visualized position.

A method for ripple-mapping visualization of bipolar intracardiac EGM amplitudes in the form of semi-transparent sails is described in U.S. patent application Ser. No. 16/228,426, filed on Dec. 20, 2018, entitled, "Electrophysiological ripple-mapping visualization method," which is assigned to the assignee of the present patent application and whose disclosure is incorporated herein by reference.

However, if there are multiple aberrant EP activations (e.g., double potentials, late potentials, fractionated signals) during a single cardiac cycle, clear visualization by ripple-mapping (e.g., in the form of sails or bars) is very difficult.

Embodiments of the present invention that are described hereinafter analyze each heart cycle to identify in the bipolar intracardiac EGM signals a primary activation and one or more secondary activations (which may or may not exist). The activation with a maximum bipolar intracardiac EGM absolute value (peak to peak) is assumed to be the primary activation; all other activation(s) are the secondary activations. Depending on the activation being primary or secondary, a processor represents, on the 3D rendering, a first type of visual indicator or a second type of visual indicator, respectively. Visual indicator types may comprise, for example, small geometrical shapes (e.g., dots, small squares), and the shapes may have different colors. As another example, visual indicators may possess other distinctive appearances, such as modes of blinking, according to whether a primary activation bipolar intracardiac EGM value or a secondary activation bipolar intracardiac EGM value is detected. For clarity a physician may choose to present just one activation on the map at any given time.

By way of example, in an embodiment, the disclosed method uses small dots that become blue whenever there is a secondary activation and become white whenever there is a primary activation (or any other colors the physician chooses).

Typically, the processor is programmed in software containing a particular algorithm that enables the processor to conduct each of the processor related steps and functions outlined above.

The disclosed visualization technique to overlay bipolar intracardiac EGM activation data on 3D cardiac anatomy with visual indicators, such as dots, of different visual forms according to type of activation, enables a physician to easily see tissue locations demonstrating aberrant behavior, such as fractionated EP signals, double EP potentials, and late EP potentials.

Easing visualization of aberrant tissue locations in the heart that require the special attention of the physician may therefore improve the diagnostic value of catheter-based EP mapping procedures.

System Description

FIG. 1 is a schematic, pictorial illustration of a cardiac three-dimensional (3D) navigation and electrophysiological (EP) signal analysis system 20, in accordance with an embodiment of the present invention. System may be configured to analyze substantially any physiological parameter or combinations of such parameters. In the description herein, by way of example, the signals analyzed are assumed to be bipolar intracardiac EGM and/or extra-cardiac (body surface) electrocardiogram (ECG) potential-time relationships. In order to fully characterize such relationships, a processor 40 uses the bipolar intracardiac EGM signals to produce an EP map, such as a local activation time (LAT) map. A method for generating an LAT map is described in U.S. Pat. No. 9,050,011, whose disclosure in fully incorporated herein by reference.

In the context of this disclosure, the term "anatomical map" refers to a map that models the 3D shape of at least a portion of the heart, and may have one or more parameters overlaid thereon. An EP map is one special case of an anatomical map, in which one or more electrophysiological parameters are overlaid. A LAT map is an example of an EP map, and thus also regarded as a type of anatomical map.

FIG. 1 shows an investigative procedure wherein system 20 measures actual electrical activity of a heart 34, using a probe 24. Typically, probe 24 comprises a catheter which is inserted into the body of patient 26 during a mapping procedure performed by a physician 28 using system 20. A distal end 32 of probe 24 is assumed to have electrodes (not shown). During the procedure, patient 26 is assumed to be attached to a grounding electrode 23. In addition, electrodes 29 are assumed to be attached to the skin of patient 26 in the region of heart 34. In an embodiment, probe 24 acquires a local bipolar intracardiac EGM as the probe moves over a portion of the heart chamber. At these instances, probe 24 location is recorded as well. The measured signals are used, as noted above and among other usages, to create an LAT map of at least part of the wall tissue of heart 34 of a patient 26.

System 20 is controlled by a system processor 40, comprising a processing unit 42 communicating with a memory 44. In some embodiments, a memory 44, which is included in system processor 40, stores an LAT and/or bipolar intracardiac EGM map 62 of at least part of wall tissue of heart 34 of patient 26. Processor 40 is typically mounted in a console 46, which comprises operating controls 38, typically including a pointing device 39 such as a mouse or trackball, used by physician 28 to interact with the processor.

Processor 40 (specifically processing unit 42) runs software comprising a probe tracker module 30, an ECG module 36, and an ECG activation-type visualization module 35, used for visualizing bipolar intracardiac EGM activations over a 3D rendering of a portion of heart 26 anatomy (i.e., in the form of dots having varying colors depending on whether activation is primary or aberrant), as described above and described in further detail below. ECG module 36 is coupled to receive actual electrical signals from electrodes 22 and electrodes 29. The module is configured to analyze the actual signals and may present the results of the analysis in a standard ECG format, typically a graphical representation moving with time, on display 48.

Probe tracker module 30 typically tracks the location of distal end 32 of probe 24 within the heart of patient 26. The tracker module may use any method for location tracking probes known in the art. For example, module 30 may operate a magnetic-field-based location tracking sub-system. (For simplicity, components of such a sub-system are not shown in FIG. 1.) Using tracker module 30, processor 40 is able to measure locations of distal end 32. In addition, using both tracker module 30 and ECG module 36, the processor is able to measure locations of the distal end, as well as LATs of the actual electrical signals detected at these particular locations.

Alternatively or additionally, tracker module 30 may track probe 24 by measuring impedances between electrode 23, electrodes 29, and electrodes 22, as well as the impedances to other electrodes which may be located on the probe. (In this case electrodes 22 and/or electrodes 29 may provide both bipolar intracardiac EGM and location tracking signals.) The Carto3® system, produced by Biosense-Webster (Irvine, Calif.), uses both magnetic field location tracking and impedance measurements for location tracking.

Results of the operations and visualizations performed by processor 40 are presented to physician 28 on a display 48, which typically presents a graphic user interface to the physician, a visual representation of the bipolar intracardiac EGM signals sensed by electrodes 22, and/or an image or map of heart 34 while it is being investigated. In an embodiment, EP activation type visualization module 35 presents to the physician a LAT map overlaid with the bipolar intracardiac EGM activations represented as dots of various colors according to the type of activation (e.g., primary or aberrant).

Processor 40 typically comprises a general-purpose computer with software programmed to carry out the functions described herein. In particular, processor 40 runs a dedicated algorithm as disclosed herein, including in FIG. 3, that enables processor 40 to perform the disclosed steps, as described below. The software run by processor 40 may be downloaded to processor 40 in electronic form, over a network, for example, or it may, alternatively or additionally, be provided and/or stored on non-transitory tangible media, such as magnetic, optical, or electronic memory.

Figure 2:
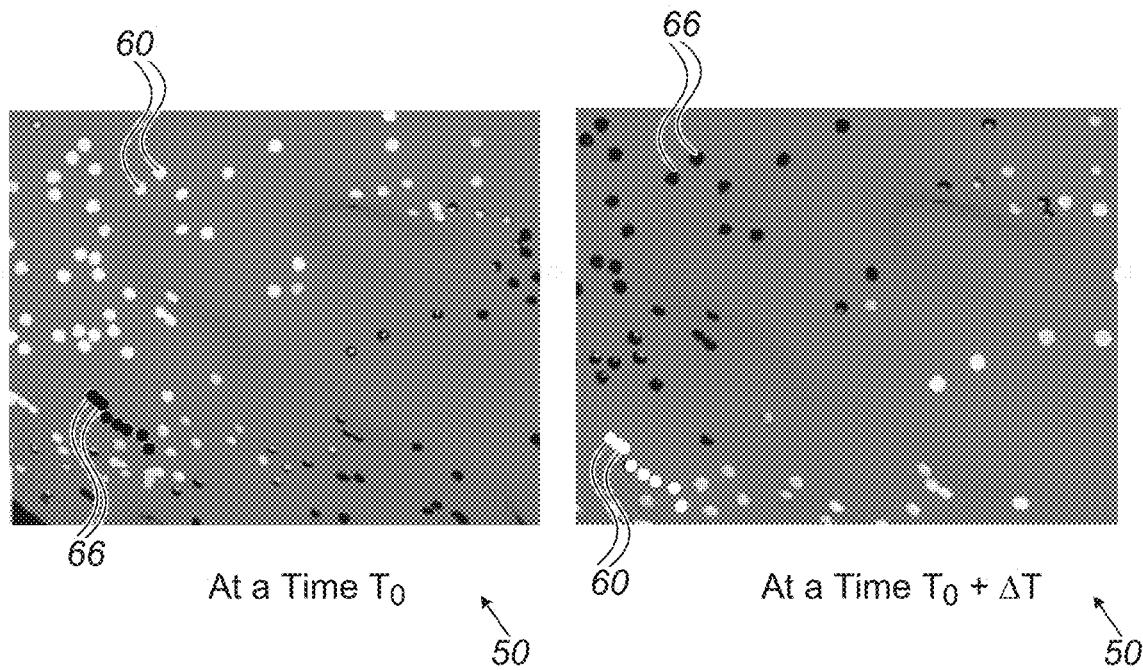
FIG. 2 is an excerpt of a volume rendering showing dot-mapping visualization of bipolar intracardiac electrogram (EGM) activation types at two consecutive times, overlaid on a portion of cardiac chamber anatomy, in accordance with an embodiment of the present invention.

Visually Differentiating Primary and Secondary Activations on Electrophysiological Maps FIG. 2 is an excerpt of a volume rendering showing dot-mapping visualization of bipolar intracardiac electrogram (EGM) activation types at two consecutive times, overlaid on a portion of cardiac chamber anatomy 50, in accordance with an embodiment of the present invention.

FIG. 2 shows two screen captures, taken at times $T_0$ and $T_0 + \Delta T$, from a displayed video (e.g., video displayed on display 48 of system 20) of a surface representation of bipolar intracardiac EGM signals according to a type of bipolar intracardiac EGM activation overlaid on the anatomical map. As seen in FIG. 2, the captured primary and aberrant patterns change within time step $\Delta T$, which is typically on the order of a fraction of a second.

In FIG. 2, the analyzed activations, visualized by dots 60 and 66, are overlaid by processor 40 on a grey-scale anatomical map, where the color of dots 60 and 66 gives an indication of the bipolar intracardiac EGM activation type at the dotted positions. In FIG. 2, white dots 60 indicate of a primary activation, whereas black dots 66 indicate of a secondary, aberrant, activation.

In some embodiments, to visualize bipolar intracardiac EGM signals as disclosed, processor 40 analyzes the bipolar intracardiac EGM signals by applying the following steps:

(i) selecting a noise level of the bipolar intracardiac EGM signal, after the bipolar intracardiac EGM signal was pre-filtered and acquired a steady baseline, (ii) labeling local maxima of the absolute value of the bipolar intracardiac EGM signal as activations whenever the peak is above the selected noise level, (iii) at every heartbeat, labeling the activation with maximum absolute value of the bipolar intracardiac EGM as the primary activation on a given visualization window-scale, labeling other activations as secondary activations, (iv) placing an initial visual indicator (e.g., black dots) on the cardiac map and changing the initial visual indicator to a first visual indicator (e.g., white dots) for locations that show primary activation, or to a second visual indicator (e.g., blue dots) for locations that show secondary activation (or to any colors or shapes the physician chooses).

In some embodiments, the noise level may be dynamically set by processor 40 according to a specific percentile of the signal (for example, the noise level may be set as the 10th percentile of the absolute value of the bipolar intracardiac EGM in a sliding window of the last 10 seconds of the bipolar intracardiac EGM signal). The noise level may be dynamically set according to the standard deviation of the absolute value of the bipolar intracardiac EGM signal over a sliding window, multiplied by a constant (for example, two times the standard deviation over a sliding window of the last 10 seconds). Activations at least as high as a specific percentage of the primary activation (for example, 90% of the primary activation) may be considered as the primary activation. If a primary and secondary activation occur at very similar times, i.e., coincide within a given number of milliseconds (for example 25 milliseconds), the secondary activation may be considered as primary (i.e., a feature in the primary activation waveform).

In an embodiment, instead of the absolute value of the bipolar intracardiac EGM signal, the processor may check the first derivative of the signal. Then the processor looks for the maximum absolute value of the derivative to differentiate between primary and secondary activations.

In some embodiments, if a primary or secondary activation coincides with a QRS complex of the bipolar intracardiac EGM waveform, it may be colored differently. The definition of "coincides with the QRS" may be within a pre-specified range in milliseconds from a respective R-wave peak. Alternatively, the QRS complex may be detected and the whole QRS time-interval may be considered. Optionally, the user may specify some range in milliseconds around the QRS complex. For example, the processor may color in yellow dots that coincide with the interval starting five milliseconds before the QRS until five milliseconds after the QRS complex.

In an embodiment, if a primary activation or a secondary activation coincides with a pacing peak, the primary or secondary activations may be colored differently. The definition of "coincides with a pacing peak" may be given as the primary or secondary activations occurring within a range of given number of milliseconds about the timing of the pacing peak.

The example dot-mapping visualization shown in FIG. 2 is chosen purely for the sake of conceptual clarity. Various additional visualization tools may apply, such as presenting the activations using another shape (e.g., diamond shape), using a magnifying glass effect to view dots 60 and 66 in detail, and others.

Figure 3:
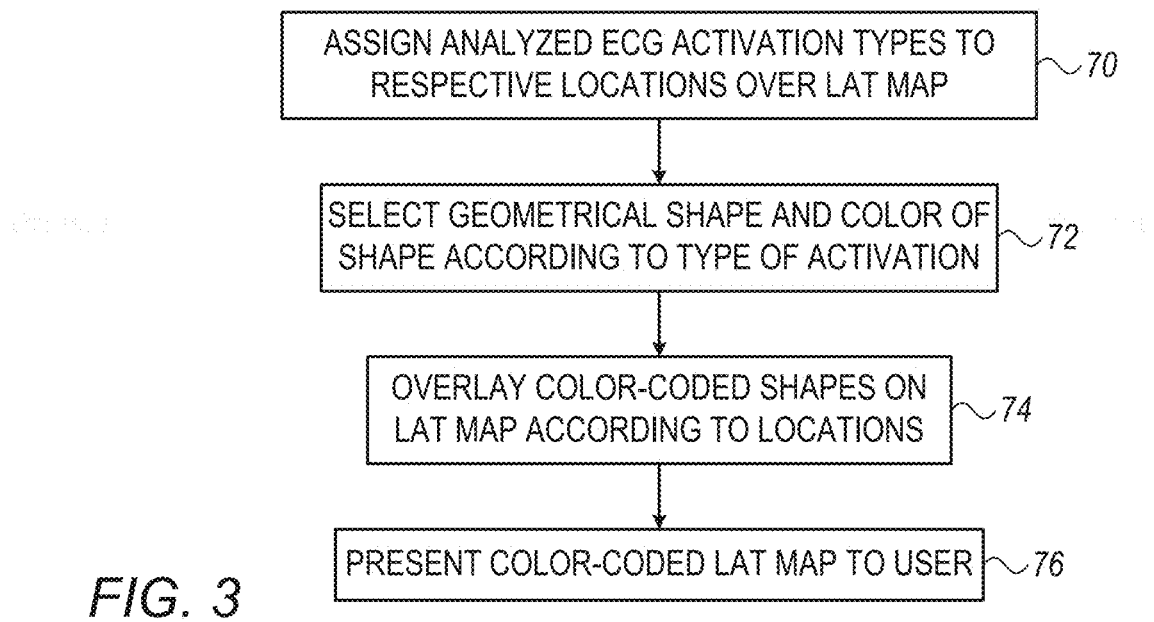
FIG. 3 is a flow chart that schematically illustrates a method and algorithm for dot-mapping visualization of bipolar intracardiac electrogram (EGM) amplitudes shown in FIG. 2, in accordance with an embodiment of the present invention.

FIG. 3 is flow chart that schematically illustrates a method for dot-mapping visualization of the bipolar intracardiac electrogram (EGM) activity type shown in FIG. 2, in accordance with an embodiment of the present invention. The algorithm, according to the presented embodiment, carries out a process that begins with processor 40 assigning bipolar intracardiac EGM activation types analyzed using steps (i)-(iv) described above, to respective locations over an anatomical map of a cardiac chamber, such as over a LAT mapped surface of cardiac chamber 50, at a bipolar intracardiac EGM activation type assigning step 70.

Next, at a shape and color selection step 72, processor 40 selects a geometrical shape and a shape color according to the type of activation (e.g., white for primary and blue for secondary). Next, processor 40 overlays the color-coded shapes on the anatomical map, according to activation type at each analyzed location, at an overlaying bipolar intracardiac EGM activation data point step 74. Finally, processor 40 presents the resulting visualization (e.g., LAT map comprising overlaid dots colored according to activation type, such as dots 60 and 66 of FIG. 2) to physician 28 on display 48, at a map displaying step 76.

The example flow chart shown in FIG. 3 is chosen purely for the sake of conceptual clarity. The present embodiment also comprises additional steps of the algorithm. Examples include additional visualizations, such as conduction arrows between dots 60 and 66. Such additional steps have been omitted from the disclosure herein purposely on order to provide a more simplified flow chart.

Although the embodiments described herein mainly address cardiac mapping, the methods and systems described herein can also be used in other applications, such as in EP mapping of a brain tissue.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for visually differentiating primary and secondary activations on electrophysiological maps, the method comprising:
   receiving an anatomical map of at least a portion of a heart;
   receiving, for at least a region of the anatomical map, positions and respective bipolar intracardiac electrogram (EGM) signals measured at the positions;
   identifying in the bipolar intracardiac EGM signals primary activations and secondary activations, wherein identifying the primary activations and the secondary activations in a bipolar intracardiac EGM signal among the bipolar intracardiac EGM signals comprises:
   selecting a noise level for the bipolar intracardiac EGM signal;
   labeling local maxima of the bipolar intracardiac EGM signal, which are above the selected noise level, as activations; and
   for a given cardiac cycle, visually labeling an activation having a maximum absolute value as a primary activation, and visually labeling other activations as secondary activations both on the anatomical map;
   deriving a surface representation of the bipolar intracardiac EGM signals over the region, including the identified primary activations and secondary activations; and
   presenting the surface representation overlaid on the anatomical map.

2. The method according to claim 1, wherein presenting the surface representation comprises presenting the primary activations using a first type of visual indicator and presenting the secondary activations using a second type of visual indicator.

3. The method according to claim 2, wherein the first and second types of the visual indicators comprise first and second different geometrical shapes.

4. The method according to claim 2, wherein the first and second types of the visual indicators have first and second different colors.

5. The method according to claim 2, wherein the first and second types of the visual indicators represent Local Activation Times (LAT).

6. A system for visually differentiating primary and secondary activations on electrophysiological maps, the system comprising:
   a memory, which is configured to store an anatomical map of at least a portion of a heart; and
   a processor, which is configured to:
      receive, for at least a region of the anatomical map, positions and respective bipolar intracardiac electrogram (EGM) signals measured at the positions;
   identify in the bipolar intracardiac EGM signals primary activations and secondary activations, wherein the processor is configured to identify the primary activations and the secondary activations in an bipolar intracardiac EGM signal among the bipolar intracardiac EGM signals, by:
      selecting a noise level for the bipolar intracardiac EGM signal;
   labeling local maxima of the bipolar intracardiac EGM signal, which are above the selected noise level, as activations; and
      for a given cardiac cycle, labeling an activation having a maximum absolute value as a primary activation, and labeling other activations as secondary activations both on the anatomical map;
   derive a surface representation of the bipolar intracardiac EGM signals over the region, including the identified primary activations and secondary activations; and
   present the surface representation overlaid on the anatomical map.

7. The system according to claim 6, wherein the processor is configured to present the surface representation by presenting the primary activations using a first type of visual indicator and presenting the secondary activations using a second type of visual indicator.

8. The system according to claim 7, wherein the first and second types of type of the visual indicators comprise first and second different geometrical shapes.

9. The system according to claim 7, wherein the first and second types of type of the visual indicators have first and second different colors.

10. The system according to claim 7, wherein the first and second types of the visual indicators represent Local Activation Times (LAT).

* * * * *